US00PP27973P2

(12) United States Plant Patent
Miyazaki

(10) Patent No.: US PP27,973 P2
(45) Date of Patent: May 2, 2017

(54) ***LOBELIA* PLANT NAMED 'SUNLOBERICOHO'**

(50) Latin Name: *Lobelia erinus*
Varietal Denomination: Sunlobericoho

(71) Applicant: SUNTORY FLOWERS LIMITED, Tokyo (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 14/998,341

(22) Filed: Jan. 4, 2016

(51) Int. Cl.
*A01H 5/02* (2006.01)

(52) U.S. Cl.
USPC ..... Plt./451

(58) Field of Classification Search
USPC ..... Plt./451
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Lobelia* plant named 'Sunlobericoho', characterized by its compact and mounding plant habit; vigorous growth habit; freely branching habit; dense and bushy plant form; freely flowering habit; long flowering period; large white-colored flowers; relative tolerance to high temperatures and good garden performance.

1 Drawing Sheet

Botanical designation: *Lobelia erinus.*
Cultivar denomination: 'SUNLOBERICOHO'.

BACKGROUND OF THE INVENTION

The present invention relates to a new and distinct cultivar of *Lobelia* plant, botanically known as *Lobelia erinus* and hereinafter referred to by the name 'Sunlobericoho'.

The new *Lobelia* plant is a product of a planned breeding program conducted by the Inventor in Higashiomi, Shiga, Japan. The objective of the breeding program is to create new compact and vigorous *Lobelia* plants with large attractive flowers and good garden performance.

The new *Lobelia* plant originated from a cross-pollination made by the Inventor in May, 2012 of a proprietary selection of *Lobelia erinus* identified as code number 11Lob-2b, not patented, as the female, or seed, parent with a proprietary selection of *Lobelia erinus* identified as code number 11Lob-10-6, not patented, as the male, or pollen, parent. The new *Lobelia* plant was discovered and selected by the Inventor as a single flowering plant within the progeny of the stated cross-pollination in a controlled greenhouse environment in Higashiomi, Shiga, Japan in May, 2013.

Asexual reproduction of the *Lobelia* plant by vegetative cuttings in Higashiomi, Shiga, Japan since May, 2013 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobericoho'. These characteristics in combination distinguish 'Sunlobericoho' as a new and distinct *Lobelia* plant:

1. Compact and mounding plant habit.
2. Vigorous growth habit.
3. Freely branching habit; dense and bushy plant form.
4. Freely flowering habit.
5. Long flowering period.
6. Large white-colored flowers.
7. Relatively tolerant to high temperatures.
8. Good garden performance.

Plants of the new *Lobelia* differ primarily from plants of the female parent selection in plant habit as plants of the new *Lobelia* are taller than plants of the female parent selection.

Plants of the new *Lobelia* differ primarily from plants of the male parent selection in flower color as plants of the male parent selection have blue and white-colored flowers.

Plants of the new *Lobelia* can be compared to plants of *Lobelia erinus* 'Sunlobecoho', disclosed in U.S. Plant Pat. No. 25,205. In side-by-side comparisons conducted in Higashiomi, Shiga, Japan, plants of the new *Lobelia* differed from plants of 'Sunlobecoho' in the following characteristics:

1. Plants of the new *Lobelia* had longer internodes than plants of 'Sunlobecoho'.
2. Plants of the new *Lobelia* had larger flowers than plants of 'Sunlobecoho'.
3. Plants of the new *Lobelia* had whiter flowers than plants of 'Sunlobecoho'.
4. Plants of the new *Lobelia* were more high temperature tolerant than plants of 'Sunlobecoho'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobericoho' grown in a container.

The photograph at the bottom of the sheet is a close-up view of a typical flowering plant of 'Sunlobericoho'.

DETAILED BOTANICAL DESCRIPTION

Plants used for the aforementioned photographs and following description were grown in 15-cm containers during the spring and early summer in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Lobelia erinus* 'Sunlobericoho'.

Parentage:

*Female, or seed, parent*.—Proprietary selection of *Lobelia erinus* identified as code number 11Lob-2b, not patented.

*Male, or pollen, parent*.—Proprietary selection of *Lobelia erinus* identified as code number 11Lob-10-6, not patented.

Propagation:

*Type cutting*.—Vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; relatively dense.

Plant description:

*Plant and growth habit*.—Compact and mounding plant habit; freely branching habit with lateral branches developing at potentially every node; dense and bushy plant habit; vigorous growth habit.

*Plant height*.—About 24 cm.

*Plant width*.—About 43 cm.

*Lateral branch description*.—Length: About 15 cm to 17 cm. Diameter: About 1.3 mm to 1.5 mm. Internode length: About 2.1 cm. Strength: Strong, flexible. Aspect: Outwardly spreading. Texture: Smooth, glabrous. Color: Close to 143A.

Leaf description:

*Arrangement*.—Alternate, simple; sessile.

*Length*.—About 2.8 cm.

*Width*.—About 4 mm.

*Shape*.—Broadly lanceolate.

*Apex*.—Obtuse.

*Base*.—Cuneate.

*Margin*.—Shallowly serrate.

*Texture and luster, upper and lower surfaces*.—Smooth, glabrous; matte.

*Venation pattern*.—Pinnate.

*Color*.—Developing leaves, upper surface: Close to 138A. Developing leaves, lower surface: Close to 138B. Fully expanded leaves, upper surface: Close to 137A; venation, close to 137B. Fully expanded leaves, lower surface: Close to 138A; venation, close to 138B.

Flower description:

*Flower arrangement, habit and shape*.—Flowers typically arranged in terminal and lateral racemes; flowers face mostly outwardly to slanting downward; freely flowering habit with about seven flowers per inflorescence and about 440 flowers developing per plant; flowers bilabiate with two upper petals and three larger lower petals.

*Fragrance*.—None detected.

*Natural flowering season*.—In Japan, plants of the new *Lobelia* flower continuously from May until October; early flowering habit, plants begin flowering about three to four weeks after planting.

*Flower longevity on the plant*.—Longevity of individual flowers is highly dependent on temperature, flowers typically last about 10 to 14 days on the plant; flowers persistent.

*Inflorescence length*.—About 15 cm.

*Inflorescence diameter*.—About 7.1 cm.

*Flower length*.—About 1.6 cm.

*Flower diameter*.—About 1.8 cm.

*Flower depth*.—About 1.7 cm.

*Flower tube length*.—About 7.9 mm.

*Flower tube diameter, mid-section*.—About 2.9 mm.

*Flower tube diameter, base*.—About 2.4 mm.

*Flower throat diameter*.—About 3.6 mm.

*Flower buds*.—Length: About 1.2 cm. Diameter: About 4.6 mm. Shape: Club-shaped. Color: Close to 2D.

*Petals*.—Arrangement: Single whorl of five petals fused towards the base; two upper petals and three larger lower petals. Upper petals: Length, beyond throat: About 6 mm. Width: About 2.7 mm. Shape: Elliptic. Apex: Acute. Margin: Entire. Texture and luster, upper and lower surfaces: Smooth, glabrous; matte. Lower petals: Length, central petal, beyond throat: About 9.8 mm. Length, lateral petals, beyond throat: About 8.3 mm. Width, central petal, beyond throat: About 5.9 mm. Width, lateral petals, beyond throat: About 6.4 mm. Shape, central and lateral petals: Obovate. Apex, central petal: Rounded. Apex, lateral petals: Cuspidate. Margin, central and lateral petals: Entire. Texture and luster, central and lateral petals, upper and lower surfaces: Smooth, glabrous; matte. Color, upper and lower petals: When opening, upper surface: Close to NN155A. When opening, lower surface: Close to 155A. Fully opened, upper and lower surfaces: Close to NN155D; color does not change with development. Fully opened, lower surface: Close to 94D; color does not change with development. Color, throat: Close to NN155D; nectar guides, close to 144D. Color, tube: Close to NN155D.

*Sepals*.—Arrangement: Single whorl of five sepals, fused at the base; star-shaped calyx. Length: About 5.9 mm. Width: About 1.6 mm. Shape: Lanceolate. Apex: Acute. Margin: Entire. Texture and luster, upper and lower surfaces: Smooth, glabrous; matte. Color, upper and lower surfaces: Close to 138A.

*Pedicels*.—Length: About 2 cm. Diameter: About 0.4 mm. Strength: Strong, flexible. Texture: Smooth, glabrous. Color: Close to 144A.

*Reproductive organs*.—Stamens: Quantity per flower: Five. Filament length: About 4.6 mm. Filament color: Close to NN155C. Anther size: About 0.5 mm by 1.9 mm. Anther shape: Elliptic. Anther color: Close to 84A. Pollen amount: Moderate. Pollen color: Close to 4D. Pistils: Quantity per flower: One. Pistil length: About 9.4 mm. Stigma shape: Globose. Stigma color: Close to 86B. Style color: Close to 144D. Ovary color: Close to 144A.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 35° C.

It is claimed:

1. A new and distinct *Lobelia* plant named 'Sunloberi-coho' as illustrated and described.

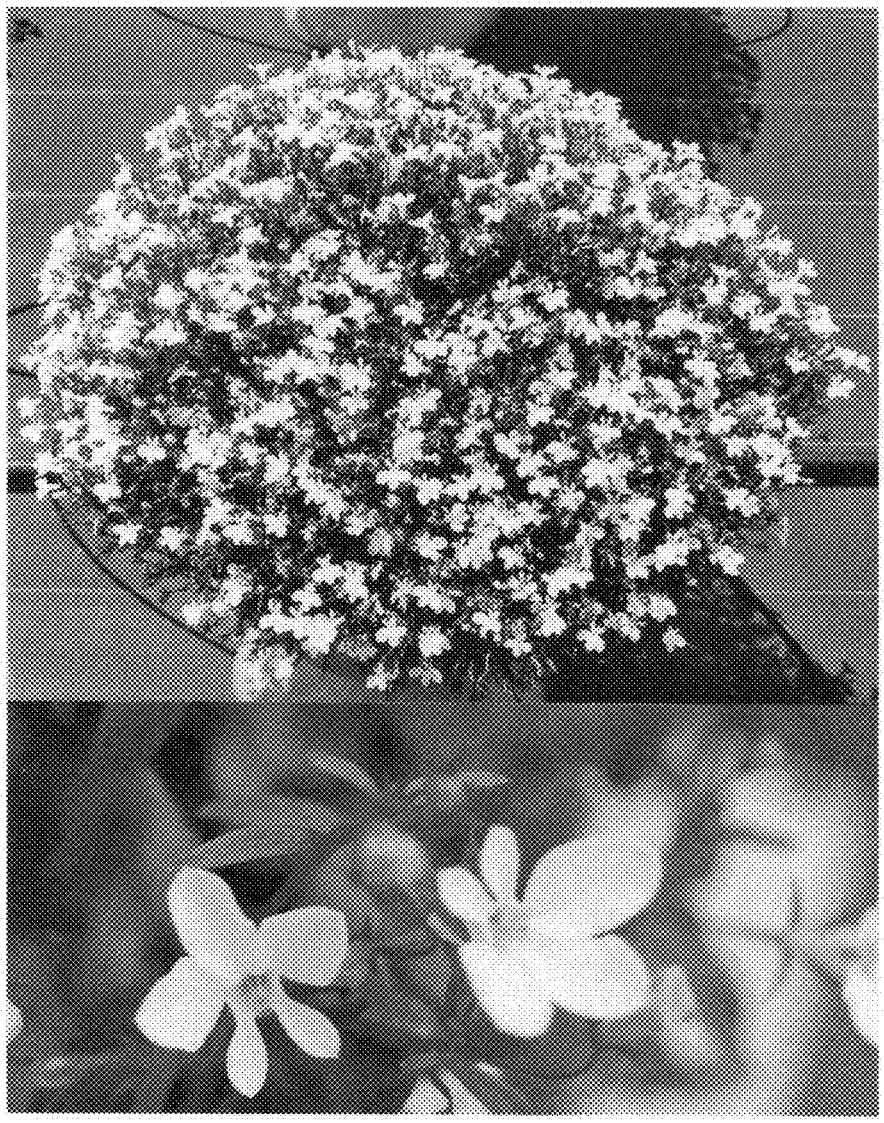

* * * * *